United States Patent
Hendriks et al.

(10) Patent No.: US 8,553,839 B2
(45) Date of Patent: Oct. 8, 2013

(54) SYSTEM AND METHOD FOR GENERATING IMAGES OF A PATIENT'S INTERIOR AND EXTERIOR

(75) Inventors: Bernardus Hendrikus Wilhelmus Hendriks, Eindhoven (NL); Adrien Desjardins, Eindhoven (NL); Drazenko Babic, Best (NL)

(73) Assignee: Koninklijke Philips N.V., Eindhoven (NL)

( * ) Notice: Subject to any disclaimer, the term of this patent is extended or adjusted under 35 U.S.C. 154(b) by 56 days.

(21) Appl. No.: 13/134,537

(22) PCT Filed: Dec. 4, 2009

(86) PCT No.: PCT/IB2009/055498
§ 371 (c)(1),
(2), (4) Date: Jun. 9, 2011

(87) PCT Pub. No.: WO2010/067281
PCT Pub. Date: Jun. 17, 2010

(65) Prior Publication Data
US 2012/0008741 A1  Jan. 12, 2012

(30) Foreign Application Priority Data
Dec. 11, 2008  (EP) .................................... 08171293

(51) Int. Cl.
*G01N 23/04* (2006.01)
(52) U.S. Cl.
USPC .......................................................... 378/63
(58) Field of Classification Search
USPC ..................................... 378/62, 63, 205, 206
See application file for complete search history.

(56) References Cited

U.S. PATENT DOCUMENTS

| | | | |
|---|---|---|---|
| 5,531,520 | A | 7/1996 | Grimson et al. |
| 5,740,802 | A | 4/1998 | Nafis et al. |
| 5,923,727 | A | 7/1999 | Navab |
| 6,088,424 | A | 7/2000 | Posethwaite et al. |

(Continued)

FOREIGN PATENT DOCUMENTS

| | | |
|---|---|---|
| CN | 221639 Y | 1/1996 |
| GB | 2433201 A | 6/2007 |

(Continued)

OTHER PUBLICATIONS

By M.A. Gennert et al. "Assessing a System to Detect Patient Motion in Spect Imaging Using Stereo Optical Cameras"; IEEE, 2003, pp. 1567-1570.

(Continued)

*Primary Examiner* — Irakli Kiknadze

(57) ABSTRACT

A system for generating an image including information of both an interior and an exterior of a patient. The system includes an X ray device for providing an X ray image of a patient's interior, and a camera responsive to a wavelength for providing a camera image of a patient's exterior. The camera may be supported by the X ray device for establishing a determined spatial relationship between the camera and the X ray device. The system further includes a spatial reference for spatially correlating the X ray image and the camera image, where the spatial reference is detectable in the X ray image and in the camera image. A data processor configured for rendering the camera image and the X ray image into a composite image on the basis of the spatial reference.

18 Claims, 5 Drawing Sheets

(56) References Cited

U.S. PATENT DOCUMENTS

| | | |
|---|---|---|
| 6,359,960 B1 * | 3/2002 | Wahl et al. .................. 378/20 |
| 6,435,717 B1 | 8/2002 | Kohler et al. |
| 6,473,489 B2 | 10/2002 | Bani-Hashemi et al. |
| 7,198,404 B2 | 4/2007 | Navab et al. |
| 7,344,307 B2 * | 3/2008 | Yatsenko et al. ............. 378/207 |
| 2002/0012420 A1 | 1/2002 | Bani-Hashemi et al. |
| 2003/0164172 A1 | 9/2003 | Chumas et al. |
| 2005/0182321 A1 | 8/2005 | Frangioni |
| 2005/0201515 A1 | 9/2005 | Mitschke |
| 2007/0041660 A1 | 2/2007 | Mahesh et al. |
| 2007/0238986 A1 | 10/2007 | Graumann |
| 2008/0130825 A1 * | 6/2008 | Fu et al. ...................... 378/8 |

FOREIGN PATENT DOCUMENTS

| | | |
|---|---|---|
| WO | 2007035907 A2 | 3/2007 |
| WO | 2007073988 A1 | 7/2007 |
| WO | 2007115825 A1 | 10/2007 |

OTHER PUBLICATIONS

By S. Krueger et al. "Modality-Integrated Magnetic Catheter Tracking for X-Ray Vascular Interventions" Physics in Medicine ad Biology; Institute of Physics Publishing, 2005, p. 1-18.

* cited by examiner

SYSTEM AND METHOD FOR GENERATING IMAGES OF A PATIENT'S INTERIOR AND EXTERIOR

CROSS-REFERENCE TO PRIOR APPLICATIONS

This application is the U.S. National Phase application under 35 U.S.C. §371 of International Application Serial No. PCT/IB2009/055498, filed on Dec. 4, 2009, which claims the benefit of European Application Serial No. 08171293.7, filed on Dec. 11, 2008. These applications are hereby incorporated by reference herein.

FIELD OF THE INVENTION

The invention relates to a system for generating an image comprising information of an interior and an exterior of a patient.

The invention further relates to a method for generating an image comprising information of an interior and an exterior of a patient.

BACKGROUND OF THE INVENTION

WO 2007/115825 discloses a device for registering an image of a tracked camera with an image provided by a tracked imaging device. For that purpose, a tracking body is attached to the tracked camera and a further tracking body is attached to the tracked imaging device. The device comprises an optical tracking system for tracking both the tracking body and the further tracking body, and for establishing a coordinate system. By tracking the tracking body attached to said camera and the further tracking body attached to the imaging device in the same coordinate system, images acquired by the camera, and images generated by the imaging device, allow for simultaneous visualization on a monitor.

SUMMARY OF THE INVENTION

Apart from being complicated to install and complex to operate, the device disclosed in WO 2007/115825 hampers an ability of a medical professional to efficiently perform a medical intervention. Namely, to enable simultaneous visualization of the images provided by the camera and the imaging device, it is required for the tracking body attached to the camera and the further tracking body attached to the imaging device, to be permanently detectable by the optical tracking system. That is, the tracking body and the further tracking body are to be visible for the optical tracking system. The latter requirement significantly limits the medical professional's freedom of action. Namely, the medical professional is to make sure that a visibility of the tracking body and the further tracking body is not obstructed by a medical professional's parts of his or hers body. Furthermore, the medical professional is to guarantee that the tracking body and the further tracking body remain located within a volume visually capturable by the optical tracking system.

It is an object of the invention to provide a system for generating an image comprising information of both an interior and an exterior of a patient, which system increases a medical professional's ability to efficiently perform a medical intervention.

This object is achieved by the system according to the invention, which system is defined in claim 1. The system according to the invention comprises an X ray device for providing an X ray image of a patient's interior and a camera responsive to a wavelength for providing a camera image of a patient's exterior. Herein the camera is supported by the X ray device for establishing a determined spatial relationship between the camera and the X ray device. The system according to the invention furthermore comprises a spatial reference for spatially correlating, i.e. correlating in spatial respect, the X ray image and the camera image. The spatial reference is detectable in both the X ray image and the camera image. The system according to the invention additionally comprises a data processor for rendering the camera image and the X ray image into a composite image on the basis of the aforementioned spatial reference. It is stressed that the camera is not necessarily an optical camera; the camera is responsive to a wavelength, which wavelength may be either in the visible spectrum, the infrared spectrum or the ultraviolet spectrum.

The system according to the invention is able to generate a composite image encompassing the X ray image and the camera image, on the basis of onetime spatially correlating of the X ray image and the camera image. Namely, since a determined spatial relationship between the camera and the X ray image is acquired through supporting the camera by the X ray device, the spatial correlation established through the spatial reference which is detectable in both the camera and the X ray image, is applicable for an indefinite time span thereafter. As a result, the need for permanently tracking the camera and the X ray device is effectively circumvented. Consequently the medical professional is enabled to efficiently perform the medical intervention. That is, the medical professional does not need to consider his or hers position with respect to the camera.

In a practical embodiment of the system according to the invention, the spatial reference includes a marker comprising at least three mutually remotely located marker points, which marker points are detectable in both the X ray image and the camera image.

In a preferred embodiment of the system according to the invention, the marker is a movable marker. This embodiment has the advantage that it increases an accuracy of the spatial correlating of the camera image and the X ray image while guaranteeing an accessibility of the surgical field for the medical professional. Namely, the spatial correlating is allowed to be performed at a location at which the medical intervention is to be carried out, i.e. the surgical field, since the marker allows for removal from the surgical field after establishing the spatial correlation.

In a further practical embodiment of the system according to the invention, the spatial reference is constitutable by a contour, or apart thereof, of the patient's exterior. This embodiment has the advantage of guaranteeing visibility of the spatial reference for practically every location and orientation of either the x ray device or the camera given the relatively large dimensions of the patient's exterior. Hence no measures need to be taken by the medical professional to prevent a loss of visibility of the spatial reference. Furthermore, in case the camera is configured for providing a stream of camera images, this embodiment is advantageous in the sense that it is robust regarding displacements of the spatial reference itself. Namely, no update of the X ray image is required for spatially correlating the X ray image and the stream of camera images in case the patient moves and consequently the spatial reference displaces since said movement is detected in the stream of camera images.

In a further practical embodiment of the system according to the invention, the camera is configured for providing a stream of camera images and the data processor is configured for rendering the stream of camera images and the X ray image into a stream of composite images on the basis of the spatial reference. This embodiment has the advantage of providing real time monitoring of the patient's exterior. The stream of composite images is preferably based on a onetime X ray image, preferably a full three dimensional reconstruction, in order to limit an exposure of both the patient and the medical professional to X rays. Nonetheless, the data processor may be additionally configured for rendering a stream of X ray images with a stream of camera images into a stream of composite images. Herein, a camera image refresh rate need not necessarily equal an X ray image refresh rate.

In a further preferred embodiment of the system according to the invention, the X ray device comprises a movable geometry, wherein the camera is supported by said movable geometry. This embodiment has the advantage that the medical professional is permitted to freely choose a patient's location or a patient's orientation with regard to the camera, since a position or a viewing angle of the camera allows for adjustment. This feature is of large assistance in generating the camera image. Additionally, this embodiment has the advantage that the stream of camera images is easily updated regarding changes in a location or an orientation of the surgical field. Namely, since the camera is attached to the X ray device, and because the camera image and the X ray image have been spatially correlated, no further spatial calibration of said images is required during a movement of the camera. Preferably, the movable geometry is embodied by a movable C arm which is usually present in X ray devices nowadays. In that way, the system according to the invention allows for seamless integration with a convenient way of working for the medical professional. Furthermore, the movable C arm has the advantage of providing an entire rotational degree of freedom for the camera with respect to the surgical area. By employing the movable C arm, the X ray image may comprise a three dimensional reconstruction.

In a further preferred embodiment of the system according to the invention, the system comprises a medical instrument being detectable in the X ray image and the stream of camera images. This embodiment has the advantage of enabling image guided surgery in a convenient and effective way. Namely, a geometry of the medical instrument is deducible by generating the onetime X ray image of both the patient and the medical instrument. As a consequence, no elaborate programming of the instrument's geometry is required. Since the medical instrument is detectable in the stream of camera images, information regarding an instrument's location and orientation, can be updated in the stream of composite images on the basis of the spatial correlation between the X ray image and the stream of camera images. Hence, through the stream of composite images the medical professional is provided with information regarding the instrument's location and orientation, both with respect to the patient's interior and exterior. Preferably, the instrument comprises pulsed Light Emitting Diodes (LEDs) for enhancing its detectability in the stream of camera images hence in the stream of composite images.

In a further practical embodiment of the system according to the invention, the system comprises a monitor for displaying the composite image. This embodiment has the advantage of providing the medical professional with visual feedback regarding the patient's interior and exterior in a simultaneous mode.

In a further preferred embodiment of the system according to the invention, the camera is configured for providing a beam of electromagnetic radiation for excitation of a contrast agent supplied to the patient. As a result, the camera image is advantageously provided with a fluorescence characteristic. The contrast agent for example comprises dyes in small molecule form, which dyes remain in a patient's blood flow for a limited amount of time, typically a few minutes. The fluorescence characteristic provides information regarding a patient's circulatory system. Preferably, the camera is arranged for providing a stream camera of images in order to generate real time information regarding the patient's blood circulatory and lymphatic systems for e.g. detecting tumors. Since the beam of electromagnetic radiation for excitation of the contrast agent is generated by the camera itself, the fluorescence characteristic is automatically spatially correlated with the X ray image by way of the spatial reference.

In a further preferred embodiment of the system according to the invention, the system comprises an illumination device arranged for projecting information comprised in the X ray image onto the patient's exterior on the basis of the spatial reference. This embodiment has the advantage that it enables the medical professional to perform the image guided medical intervention even more safely and effectively. Namely, this embodiment effectively circumvents the need for translating the composite image to the surgical field through providing information regarding the patient's interior at the patient's exterior. Preferably, the surgical field is selected for projecting information comprised in the X ray image. Preferably, a projection of information comprised in the X ray image is compensated for a possible curvature of the patient's exterior on the basis of the camera image.

In a further preferred embodiment of the system according to the invention, the illumination device is supported by the X ray device for establishing a determined spatial relationship between the illumination device and the X ray device. This embodiment has the advantage that a projection of information comprised in the X ray image is easily performed, that is, without further spatial correlating. Since the camera is supported by the X ray device as well, a determined spatial relationship between the camera and the illumination device is obtained. Because the camera image has been spatially correlated to the X ray image, information comprised in the X ray image is projected to the patient's exterior without further calibration of the illumination device.

In a further practical embodiment of the system according to the invention, the illumination device is configured for radiation sterilization. For this purpose the illumination device is arranged to transmit a beam of electromagnetic radiation, which electromagnetic radiation has a wavelength at which the electromagnetic radiation is absorbable by the DNA of infectious agents such as bacteria and other pathogenic cells. For instance, UV radiation at a wavelength of about 250 [nm] is employed. This embodiment has the advantage of being capable to sterilize an environment of the system according to the invention, e.g. a surgical table, more effectively. Namely, compared to sterilization based on solvents, the chance of successful sterilization is significantly larger. An additional advantage of this embodiment is in the fact that the sterilization is quickly and easily performed, that is, without interference of other systems. Preferably the illumination device is attached to a movable C arm comprised in the X ray device. In that case, the sterilization is performed by making a rotation, preferably a full rotation, employing the movable C arm.

In a further preferred embodiment of the system according to the invention, the system comprises a further camera responsive to a further wavelength for providing a further camera image of the patient's exterior. Herein, the further camera image has a further parallax which differs from a parallax of the camera image. As a result, a three dimensional camera image is obtained. The further camera is supported by the X ray device for establishing a determined spatial relationship between the further camera and the X ray device.

Furthermore, a further data processor is arranged for rendering the further camera image and the composite image into a further composite image on the basis of the spatial reference, which spatial is detectable in the further camera image. This embodiment has the advantage of generating more detailed information regarding the patient's exterior through providing a three dimensional camera image.

In a further preferred embodiment of the system according to the invention, the camera is arranged for providing a stream of camera images, the further camera is arranged for providing a stream of further camera images and the further data processor for detecting a movement of the contour, or a part thereof, of the patient's exterior and for subsequently updating the X ray image according to said movement. This embodiment has the advantage of providing real time three dimensional monitoring of the patient's exterior and accordingly updating the X ray image of the patient's interior, while exposing the patient to a minimum amount of X rays. Namely, by spatially correlating the patient's contour in the stream of camera images and the X ray image, the onetime X ray image is updated in conformance with a movement of the contour of a patient's exterior as detected by the further data processor.

It is a further object of the invention to provide a method generating an image comprising information of both an interior and an exterior of a patient, which method increases a medical professional's ability to efficiently perform a medical intervention. This object is achieved by the method according to the invention as defined in claim 13. The method according to the invention comprises a step of providing an X ray image of a patient's interior by an X ray device and a step of providing a camera image of a patient's exterior by a camera responsive to a wavelength, wherein the camera is supported by the X ray device. The method according to the invention furthermore comprises a step of spatially correlating the X ray image and the camera image by a spatial reference wherein the spatial reference is detectable in the X ray image and in the camera image. The method furthermore comprises a step of rendering the camera image and the X ray image into a composite image on the basis of the spatial reference by a data processor.

The method according to the invention generates a composite image encompassing the X ray image and the camera image, on the basis of onetime spatially correlating of the X ray image and the camera image. Namely, since a determined spatial relationship between the camera and the X ray image is acquired through supporting the camera by the X ray device, the spatial correlation established through the spatial reference which is detectable in both the camera and the X ray image, is applicable for an indefinite time span thereafter. As a result, the need for permanently tracking the camera and the X ray device is effectively circumvented. The onetime spatial correlating clearly enhances the convenience for performing the method by the medical professional.

In a preferred embodiment of the method according to the invention, the method comprises a step of providing a beam of electromagnetic radiation by the camera for excitation of a contrast agent supplied to a patient. As a result, the method is advantageously capable of generating a fluorescence image. Preferably, the step of providing the beam of electromagnetic radiation for excitation of the contrast agent is followed by a step of rendering the fluorescence image with the composite image through the data processor into a composite fluorescence image.

In a practical embodiment of the method according to the invention, the method comprises a step of displaying the composite image on a monitor. This step advantageously provides the medical professional with visual feedback regarding the patient's interior and exterior in a simultaneous mode.

In a further preferred embodiment of the method according to the invention, the method comprises a step of selecting information from the X ray image and a step of projecting said information onto the patient's exterior by an illumination device on the basis of the spatial reference. This step embodiment has the advantage that it enables the medical professional to perform the image guided medical intervention even more safely and effectively. Namely, this step effectively circumvents the need for translating the composite image to the surgical field through providing information regarding the patient's interior at the patient's exterior. As a result, the medical professional is enabled to easily find the best location on the patient's exterior to position for example surgical instruments. Consequently, patient trauma is minimized and therapeutic efficacy is enlarged.

In a further preferred embodiment of the method according to the invention, the method comprises a step of radiation sterilization performed by the illumination device. For this purpose the illumination device is arranged to transmit a beam of electromagnetic radiation, which electromagnetic radiation has a wavelength at which the electromagnetic radiation is absorbable by the DNA of infectious agents such as bacteria and other pathogenic cells, e.g. a wavelength of about 250 [nm]. This embodiment is advantageously capable of quickly sterilizing an environment of the X ray device, e.g. in between interventions carried out employing the X ray device or during night.

In a further preferred embodiment of the method according to the invention, the method comprises a step of providing an X ray image of a medical instrument and a step of localizing the medical instrument by detecting the medical instrument in the X ray image and in the camera image. This embodiment has the enabling image guided surgery in an efficient manner. Namely, the need for programming a geometry of the medical instrument is effectively circumvented by generating an X ray image of the medical instrument. Preferably, the geometry of the medical instrument is recorded by making a full rotation with a moveable C arm geometry comprised in nowadays X ray devices.

In a further practical embodiment of the method according to the invention, the step of providing the X ray image is performed by rotating a rotatable geometry comprised in the X ray device. This step has the advantage of being compliant with the common way of working for a medical professional using a nowadays X ray device.

In a further preferred embodiment of the method according to the invention, the method comprises a step of providing a further camera image of a patient's exterior by a further camera responsive to a further wavelength, wherein the further camera is supported by the X ray device. This embodiment furthermore comprises a step of spatially correlating the X ray image and the further camera image by the spatial reference, which spatial reference is detectable in the further camera image and which spatial reference for example includes a movable marker, and a step of rendering the further camera image and the composite image into a further composite image on the basis of the spatial reference by a further data processor. The method further comprises a step of spatially correlating a patient's contour in the X ray image, in the camera image and in the further camera image. Subsequently, the method comprises a step of detecting a movement of the patient's contour by the further data processor, and a step of updating the X ray image according to said movement on the basis of the spatially correlating of the patient's contour. This embodiment has the advantage of being robust regarding a conceivable movement of the patient since the movement of the patient is compensated for in the composite image without providing an additional X ray image. Hence, a patient's exposure to X rays is kept at a minimum level.

Applications of the system and the method according to the invention are in image guided medical interventions such as surgery and insertion of needles and catheters.

DETAILED DESCRIPTION OF THE EMBODIMENTS

Figure 1:
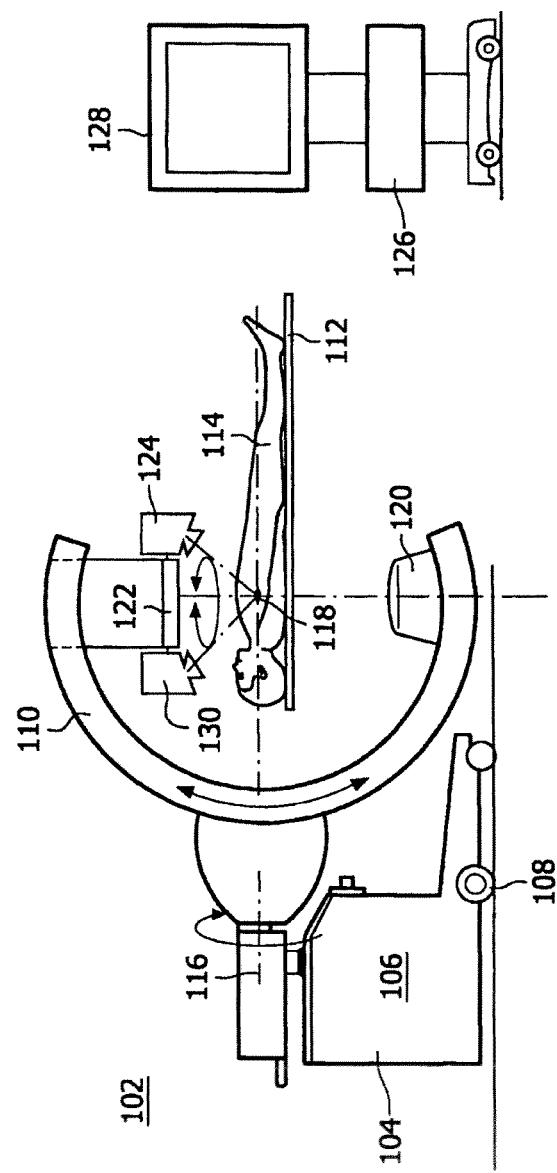
FIG. 1 schematically displays a first embodiment of the system according to the invention comprising an illumination device.
Figure 2:
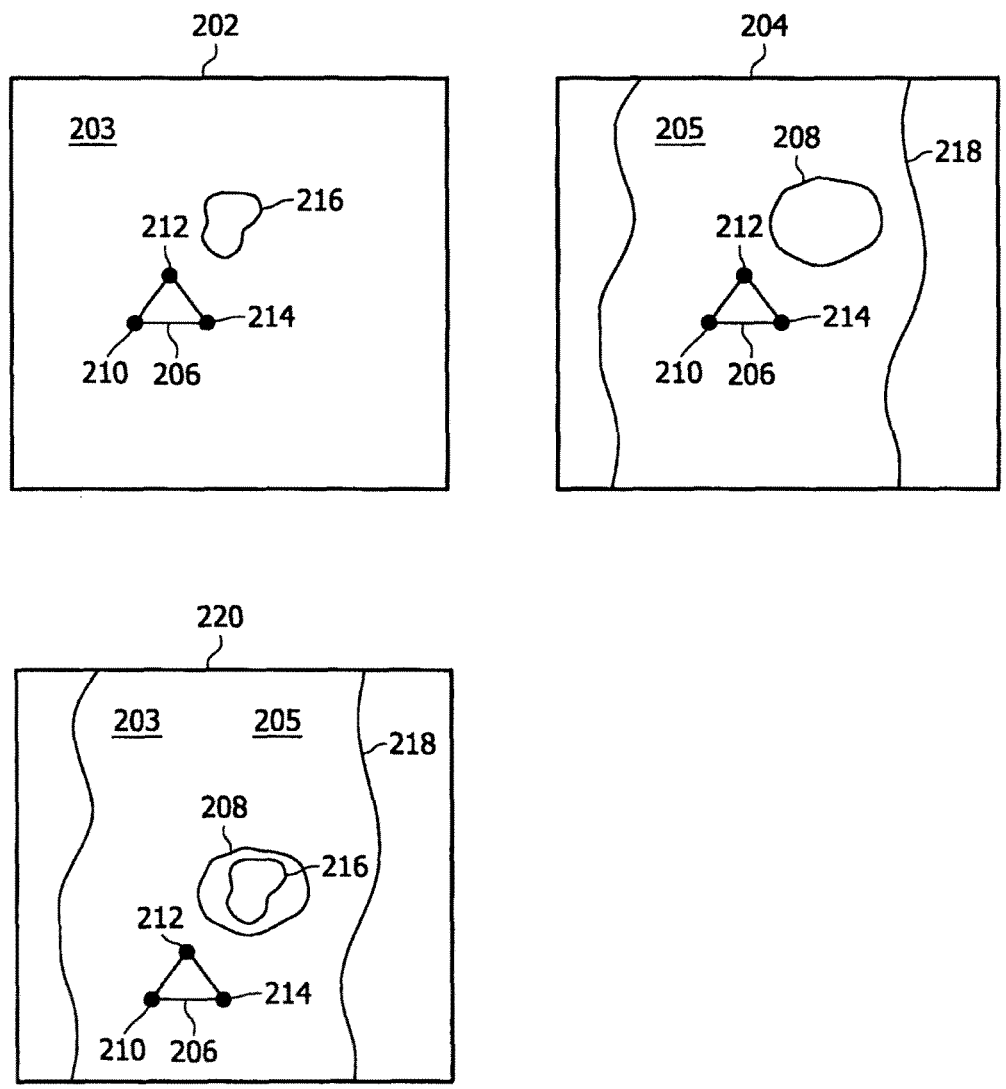
FIG. 2 schematically shows an X ray image, a stream of camera images and a stream of composite images as generated by the embodiment displayed in FIG. 1.

FIG. 1 schematically displays a system 102 comprising an X ray device 104 for providing an X ray image 202 of a patient's interior 203, as displayed in FIG. 2. The X ray device 104, see FIG. 1, has a base frame 106 supported by wheels 108, a movable C arm 110 and a surgical table 112 for supporting a patient 114, which patient 114 is a human being in this particular example. The C arm 110 is rotatable with regard to an axis 116, which axis 116 has a direction corresponding to a main orientation of the surgical table 112, and to an axis 118, which axis 118 is perpendicular to the axis 116 and parallel to the surgical table 112. An X ray source 120 and an X ray detector 122, which is preferably a rectangular and flat detector, are mounted on the C arm 110 such that the X ray source and the X ray detector reside opposite one another with respect to the axis 118. A camera 124 for providing a stream of camera images 204 of a patient's exterior 205, as displayed in FIG. 2, is mounted on the C arm 110 aside the X ray detector 122. In this specific example, the camera 124 is sensitive to wavelengths in the visible spectrum.

Referring to FIG. 2, a movable marker 206 is installed on the patient's exterior 205 near the surgical field 208 for spatially correlating the X ray image 202 and the stream of camera images 204. The movable marker 206 comprises three points 210, 212 and 214, which points are displayed in both the X ray image 202 and the stream of camera images 204. In this example, the X ray image 202 furthermore displays a tumor 216 present in the interior 203 of the patient 114. The stream of camera images 204 additionally displays a body contour 218 of the patient 114. Through connecting the points 210, 212 and 214 in the X ray image 202 with said points in the stream of camera images 204, the X ray image 202 and the stream of camera images 204 allow for spatially correlating. Referring to FIG. 1, a data processor 126 renders the X ray image 202 and the stream of camera images 204 into a stream of composite images 220 based on the spatial correlating provided by the movable marker 206. The stream of composite images 220 display the patient's interior 203 and the patient's exterior 205 in a geometrically overlapping sense, and furthermore the moveable marker 206, the surgical field 208, the tumor 216 and the patient's body contour 218.

The camera 124 is configured for providing a beam of electromagnetic radiation for excitation of a contrast agent supplied to the patient 114 in order to provide the stream of camera images 204 and consequently the stream of composite images 220 with a fluorescence characteristic. A monitor 128, as depicted in FIG. 1, displays the stream of composite images 220 to a medical professional (not shown). The system 102 furthermore comprises an illumination device 130 mounted on the C arm 110 aside the X ray detector 122, hence aside to the camera 124. The illumination device 130 is configured for projecting information comprised in the X ray image 202, for example the tumor 214, on the patient's exterior 205. The illumination device 130 is further arranged for radiation sterilization of e.g. the surgical table 112 and its environment, by way of transmitting a beam of electromagnetic radiation having a wavelength at which the electromagnetic radiation is absorbable by the DNA of infectious agents. In this particular example, a wavelength of about 250 [nm] is employed. The sterilization of the surgical table 112 is performed in between interventions performed at the system 102, by making a preferably full rotation with the C arm 110.

Figure 3:
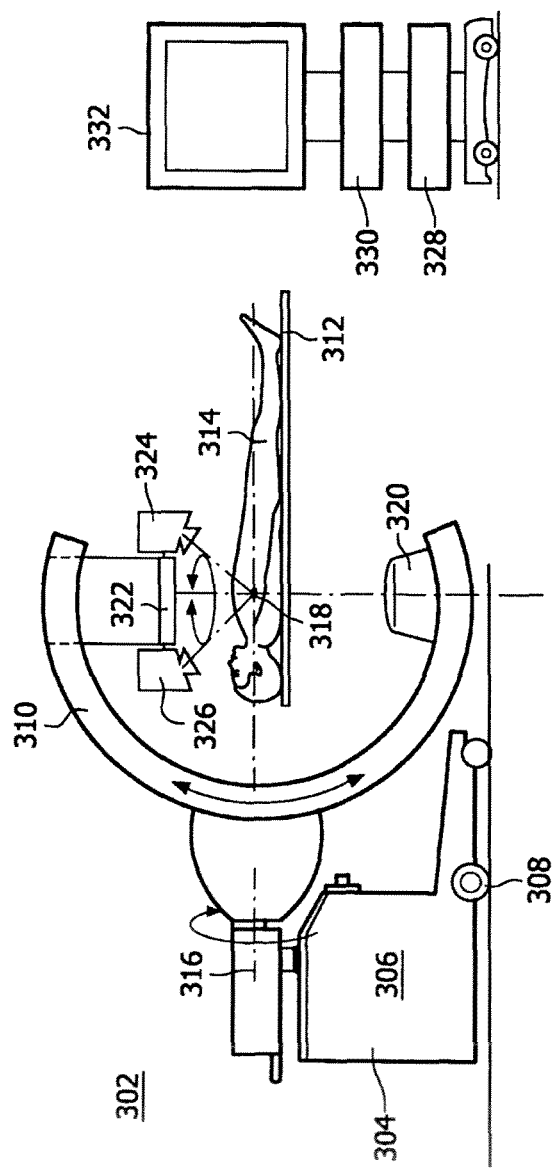
FIG. 3 schematically depicts a second embodiment of the system according to the invention comprising a further camera.
Figure 4:
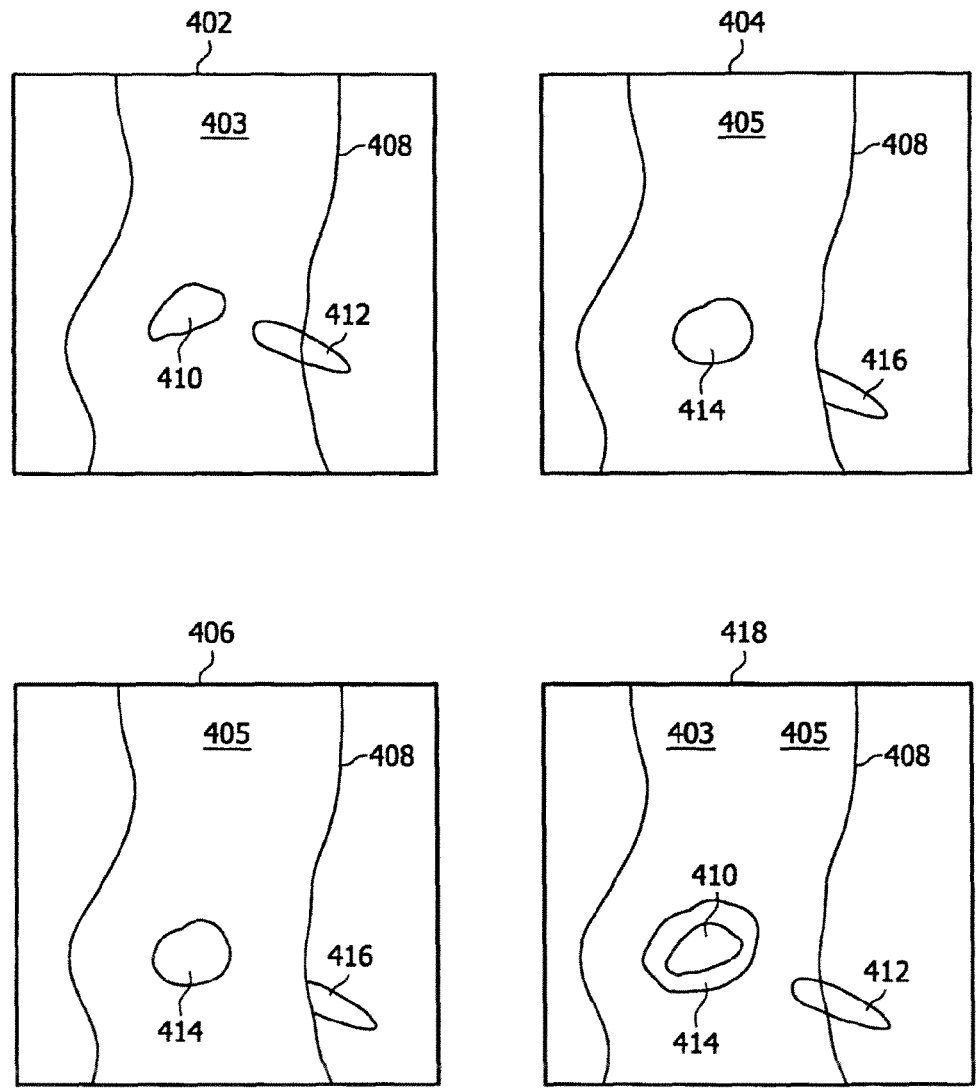
FIG. 4 schematically an X ray image, a stream of camera images, a stream of further camera images and a further stream of composite images as generated by the embodiment displayed in FIG. 3.

FIG. 3 schematically displays a system 302 comprising an X ray device 304 for providing an X ray image 402 of a patient's interior 403, as displayed in FIG. 4. The X ray device 304, see FIG. 3, has a base frame 306 supported by wheels 308, a movable C arm 310 and a surgical table 312 for supporting a patient 314. In this particular example, the patient 314 is a human being. The C arm 310 is rotatable with regard to the axis 316, which axis 316 has a direction corresponding to a main orientation of the surgical table 312, and to an axis 318, which axis 318 is perpendicular to the axis 316 and parallel to the surgical table 312. and to the axis 318. An X ray source 320 and an X ray detector 322, which is preferably a rectangular and flat detector, are mounted on the C arm 310 such that the X ray source and the X ray detector reside opposite one another with respect to the axis 318. A camera 324 for providing a stream of camera images 404 of a patient's exterior 405, as depicted in FIG. 4, is mounted on the C arm 310 aside the X ray detector 322. A further camera 326 for providing a further stream of camera images 406 of the patient's exterior 405, as displayed in FIG. 4, is additionally mounted on the C arm 310 aside the X ray detector 322. The camera 324 is responsive to a wavelength in the visible spectrum while the further camera 326 is responsive to a further wavelength. In this specific example, both the wavelength and the further wavelength are in the visible spectrum.

Referring to FIG. 4, the X ray image 402 displays the patient's interior 403, a contour 408 of the patient's exterior 405, a tumor 410 or another medical deficiency present in the interior 403 of the patient 314, and a medical instrument 412, which medical instrument is partly present in the patient's interior 403 in this particular example. For the purpose of displaying the contour 408, an amount of X ray radiation provided by the X ray source 320 to the patient 314 must be sufficiently large, i.e. the amount of X ray radiation is to enable a detectability of a patient's soft tissue in the X ray image 402. The stream of camera images 404 and the stream of further camera images 406 display the patient's exterior 405, the contour 408 of the patient's exterior 405, a surgical field 414 and a part 416 of the medical instrument 412, which part 416 is not present in the patient's interior 403. Through connecting the contour 408 of the patient's exterior 405 in the X ray image 402 with said contour in the stream of camera images 404 and in the stream of further camera images 406, the X ray image 402, the stream of camera images 404 and the stream of further camera images 406 allow for spatially correlating.

Referring to FIG. 3, a data processor 328 renders the X ray image 402 and the stream of camera images 404 into a stream of composite images (not shown) based on the spatial correlating provided by the contour 408 of the patient's exterior 405. A further data processor 330 renders the stream of composite images (not shown) with the stream of further camera images 406 into a further stream of composite images 418 on the basis of the spatial correlating provided by the contour 408 of the patient's exterior 405. The further stream of composite images 418 display the patient's interior 403 and the patient's exterior 405 in a geometrically overlapping sense, and furthermore the contour 408 of the patient's exterior 405, the tumor 410, the medical instrument 412 and the surgical field 414. For generating a three dimensional further stream of composite images 418, the camera 324 has a parallax which differs from a further parallax of the further camera 326. The further data processor 330 is additionally configured for detecting a movement of the patient's contour 408, and for subsequently updating the X ray image 402 and hence the further stream of composite images 418 in accordance with said movement. As depicted in FIG. 3, a monitor 332 displays the further stream of composite images 418 to a medical professional (not shown).

Figure 5:
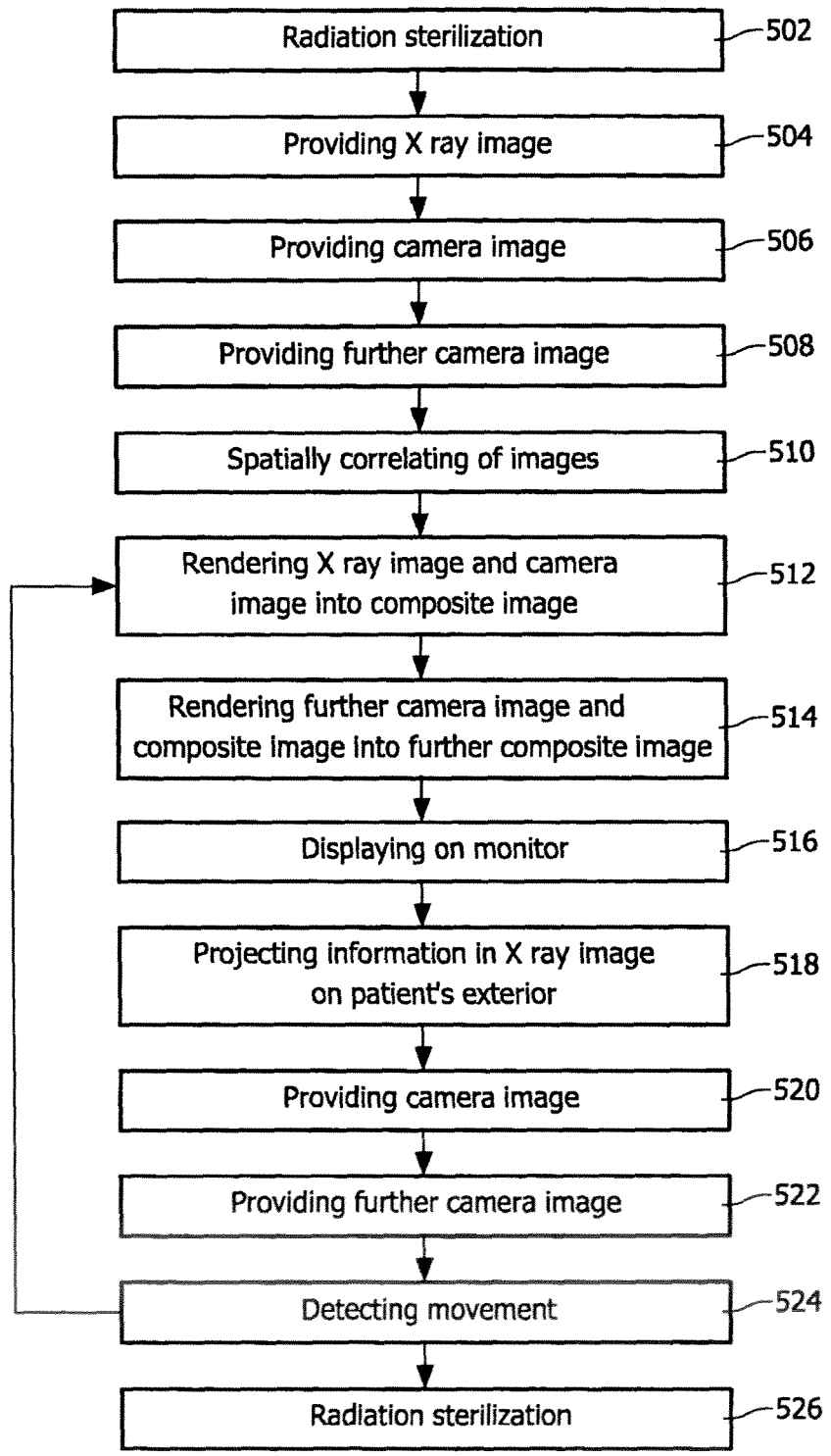
FIG. 5 schematically shows an embodiment of the method according to the invention by way of a flowchart.

FIG. 5 schematically depicts an embodiment of the method according to the invention by way of a flowchart. The method comprises a step 502 of radiation sterilization by an illumination device mounted on an X ray device, prior to performing a medical intervention at the X ray device. The method subsequently comprises a step 504 of providing an X ray image of a patient's interior by the X ray device, a step 506 of providing a camera image of a patient's exterior by a camera mounted on a movable C arm or the like of the X ray device and a step 508 of providing a further camera image of the patient's exterior through a further camera attached to said C arm. The method furthermore comprises a step 510 of spatially correlating the X ray image, the camera image and the further camera image by way of a spatial reference. Next, a step 512 is comprised for rendering the X ray image and the camera image into a composite image by way of a data processor on the basis of the spatial reference. Hereafter, a step 514 is included for subsequently rendering the further camera image and the composite image into a further composite image by way of a further data processor on the basis of said spatial reference. In a step 516 the further composite image is displayed to a medical professional by way of a monitor. A step 518 is comprised for projecting information comprised in the X ray image, such as a tumor, on the patient's exterior. In steps 520 and 522, the camera image and the further camera image are being refreshed, respectively. Hereafter, in step 524, a movement of the patient's contour is detected. Subsequently, in step 512 the composite image is updated regarding said movement. The method comprises a final step 526, i.e. after performing the medical intervention at the X ray device, which step 526 provides radiation sterilization by the illumination device mounted on the X ray device.

While the invention has been illustrated and described in detail in the drawings and in the foregoing description, the illustrations and the description are to be considered illustrative or exemplary and not restrictive. The invention is not limited to the disclosed embodiments. For instance, to increase an accuracy of spatial correlating of the camera image and the X ray image, a plurality of movable markers may be employed. It is noted that the system according to the invention and all its components can be made by applying processes and materials known per se. In the set of claims and the description the word "comprising" does not exclude other elements and the indefinite article "a" or "an" does not exclude a plurality. Any reference signs in the claims should not be construed as limiting the scope. It is further noted that all possible combinations of features as defined in the set of claims are part of the invention.

The invention claimed is:

1. A system for generating an image comprising information of an interior and an exterior of a patient, the system comprising:
    an X ray device for providing an X ray image of a patient's interior,
    a camera responsive to a wavelength for providing a camera image of a patient's exterior, the camera being supported by the X ray device for establishing a determined spatial relationship between the camera and the X ray device,
    a spatial reference for spatially correlating the X ray image and the camera image, the spatial reference being detectable in the X ray image and in the camera image, and
    a data processor for rendering the camera image and the X ray image into a composite image on the basis of the spatial reference, wherein the spatial reference includes a movable marker for increasing an accuracy of the spatially correlating, the movable marker being installed on the patient's exterior near a surgical field that corresponds to a location at which a medical intervention is to be carried out, wherein the movable marker comprises at least three mutually remotely located marker points, wherein the three mutually remotely located marker points are detectable and displayed in both the X ray image and in the camera image, further wherein the spatially correlating is enabled through connecting the three mutually remotely located marker points in the X ray image with corresponding marker points in the camera image, further wherein the movable marker allows for removal from the surgical field after establishing a spatial correlation.

2. The system according to claim 1, further wherein the spatial reference is constitutable by a contour, or a part thereof, of the patient's exterior.

3. The system according to claim 1, wherein the camera is configured for providing a stream of camera images and wherein the data processor is configured for rendering the stream of camera images and the X ray image into a stream of composite images on the basis of the spatial reference.

4. The system according to claim 3, comprising an instrument for performing a medical intervention, the instrument being detectable in the X ray image and in the stream of camera images.

5. The system according to claim 1, wherein the X ray device comprises a movable geometry and wherein the camera is supported by said movable geometry.

6. The system according to claim 1, comprising a monitor for displaying the composite image.

7. The system according to claim 1, wherein the camera is configured for providing a beam of electromagnetic radiation for excitation of a contrast agent supplied to a patient.

8. The system according to claim 1, comprising an illumination device arranged for projecting information comprised in the X ray image onto the patient's exterior on the basis of the spatial reference.

9. The system according to claim 8, wherein the illumination device is supported by the X ray device for establishing a determined spatial relationship between the illumination device and the X ray device.

10. The system according to claim 8, wherein the illumination device is configured for radiation sterilization.

11. The system according to claim 1, comprising:
a further camera responsive to a further wavelength for providing a further camera image of the patient's exterior, the further camera having a further parallax which differs from a parallax of the camera, the further camera being supported by the X ray device for establishing a determined spatial relationship between the further camera and the X ray device,
a further data processor arranged for rendering the further camera image and the composite image into a further composite image on the basis of the spatial reference which is detectable in the further camera image.

12. The system according to claim 11, wherein the camera is arranged for providing a stream of camera images, wherein the further camera is arranged for providing a stream of further camera images, and wherein the further data processor is arranged for detecting a movement of the contour, or a part thereof, of the patient's exterior and for subsequently updating the X ray image according to said movement.

13. A method for generating an image comprising information of an interior and an exterior of a patient, the method comprising act of:
providing an X ray image of a patient's interior by an X ray device,
providing a camera image of a patient's exterior by a camera responsive to a wavelength, the camera being supported by the X ray device,
spatially correlating the X ray image and the camera image by a spatial reference, the spatial reference being detectable in the X ray image and in the camera image, and
of rendering the camera image and the X ray image into a composite image on the basis of the spatial reference by a data processor, wherein the spatial reference includes a movable marker for increasing an accuracy of the spatially correlating, the movable marker being installed on the patient's exterior near a surgical field that corresponds to a location at which a medical intervention is to be carried out, wherein the movable marker comprises at least three mutually remotely located marker points, wherein the three mutually remotely located marker points are detectable and displayed in both the X ray image and in the camera image, further wherein the spatially correlating is enabled through connecting the three mutually remotely located marker points in the X ray image with corresponding marker points in the camera image, further wherein the movable marker allows for removal from the surgical field after establishing a spatial correlation.

14. The method according to claim 13, comprising an act of displaying the composite image on a monitor.

15. The method according to claim 13, further comprising an act of selecting information from the X ray image and a step of projecting said information onto the patient's exterior by an illumination device on the basis of the spatial reference.

16. The method according to claim 15, further comprising an act of radiation sterilization performed by an illumination device.

17. The method according to claim 13, wherein the act of providing the X ray image is performed by rotating a rotatable geometry comprised in the X ray device.

18. The method according to claim 13, further comprising acts of:
providing a further camera image of a patient's exterior by a further camera responsive to a further wavelength, the further camera being supported by the X ray device,
spatially correlating the X ray image and the further camera image by the spatial reference, which spatial reference is detectable in the further camera image,
rendering the further camera image and the composite image into a further composite image on the basis of the spatial reference by a further data processor,
spatially correlating a patient's contour in the X ray image, in the camera image and in the further camera image,
detecting a movement of the contour of the patient's exterior by the further data processor, and
updating the X ray image according to said movement on the basis of the spatially correlating of the patient's contour.

* * * * *